United States Patent [19]

Williams et al.

[11] Patent Number: 5,059,417

[45] Date of Patent: Oct. 22, 1991

[54] PEROXIDE GEL DENTIFRICE

[75] Inventors: David R. Williams, Monroe; Christine W. Ryles, Milford, both of Conn.

[73] Assignee: Chesebrough-Pond's USA Co., Division of Conopco, Inc., Greenwich, Conn.

[21] Appl. No.: 544,306

[22] Filed: Jun. 26, 1990

[51] Int. Cl.$^5$ .................. A61K 7/20; A61K 33/40
[52] U.S. Cl. .................. 424/53; 424/616
[58] Field of Search .................. 424/53, 616

[56] References Cited

U.S. PATENT DOCUMENTS

| | | | |
|---|---|---|---|
| 3,577,521 | 5/1971 | Scheller | 424/55 |
| 3,639,574 | 2/1972 | Schmolka | 424/78 |
| 4,130,501 | 12/1978 | Lutz et al. | 252/186 |
| 4,226,851 | 10/1980 | Sompayrac | 424/53 |
| 4,302,441 | 11/1981 | Muhlemann et al. | 424/48 |
| 4,343,785 | 8/1982 | Schmolka | 424/49 |
| 4,431,631 | 2/1984 | Clipper et al. | 424/53 |
| 4,465,663 | 8/1984 | Schmolka | 424/62 |
| 4,528,180 | 7/1985 | Schaeffer | 424/52 |
| 4,537,778 | 8/1985 | Clipper et al. | 424/53 |
| 4,684,517 | 8/1987 | Clipper et al. | 424/53 |
| 4,696,757 | 9/1987 | Blank et al. | 424/53 |
| 4,788,052 | 11/1988 | Ng et al. | 424/53 |
| 4,837,008 | 6/1989 | Rudy et al. | 424/53 |
| 4,839,156 | 6/1989 | Ng et al. | 424/53 |
| 4,839,157 | 6/1989 | Mel-King Ng et al. | 424/53 |
| 4,849,213 | 7/1989 | Schaeffer | 424/53 |
| 4,895,721 | 1/1990 | Drucker | 424/53 |

OTHER PUBLICATIONS

Periodontics and Oral Higiene, Keyes et al, Jan. 1978, pp. 51-56.

Primary Examiner—Shep K. Rose
Attorney, Agent, or Firm—Milton L. Honig

[57] ABSTRACT

An oral composition is provided in the form of a clear gel dentifrice containing hydrogen peroxide and a polyoxyethylene-poloxypropylene copolymer. The gel is stabilized against loss of viscosity at low temperatures by the presence of glycerol in amounts more than 30% but less than 50%. The weight ratio of glycerol to copolymer must range from 1:0.7 to 1:0.4. Advantageously for peroxide stability, the composition has a pH of less than 3. Phosphoric acid is beneficial as the acidifying agent.

12 Claims, No Drawings

PEROXIDE GEL DENTIFRICE

BACKGROUND OF THE INVENTION

1. Field of the Invention

The invention relates to a gel dentifrice containing peroxide and a viscosity stabilization system.

2. The Related Art

Aqueous hydrogen peroxide is widely viewed by the dental profession as an effective treatment against gum disease. Periodontal disorders are believed to arise from infectious anaerobic microorganisms which are active in the absence of oxygen. These microorganisms can be controlled or entirely eliminated by contact with peroxides which release oxygen. According to this rationale, oxygen creates an aerobic atmosphere destructive to the microorganisms.

Facile reactivity of the peroxide benefits performance but conversely results in storage stability problems. Dentifrices containing peroxides tend to decompose within a relatively short period of time. Not only is activity lost but there can be a marked breakdown in the dentifrice's physical properties. Dentrifice viscosity is particularly adversely affected by the chemical breakdown of thickening agents. A variety of techniques have been developed to counter the problem. U.S. Pat. No. 4,226,851 (Sompayrac) discloses oral compositions comprising hydrogen peroxide and zinc chloride wherein vitamin E is added as a stabilizing agent. U.S. Pat. No. 4,788,052 and U.S. Pat. No. 4,839,157 both to Ng et al. report stable aqueous hydrogen peroxide gel dentifrices stabilized with a combination of hydrophilic and hydrophobic fumed silica. These gels include polyethylene glycol, sodium saccharin, sodium benzoate, polyethylene oxide type nonionic surfactant and flavor all maintained at a pH of 3–6, preferably 4.5–5, through acidification with phosphoric or citric acids. A related patent, U.S. Pat. No. 4,839,156 (Ng et al), further specifies use of polyoxyethylene-polyoxypropylene block copolymers, polyethylene glycol, nonionic surfactant and flavour. Again citric or phosphoric acids maintain a pH of about 4.5 to 6.

Stability may also be enhanced by employing relatively non-reactive components. For instance, U.S. Pat. No. 4,684,517, U.S. Pat. No. 4,537,778 and U.S. Pat. No. 4,431,631 all to Clipper et al report wintergreen and cinnamon flavors as being non-reactive in peroxide oral preparations. Other components include 1–20% polyhydric alcohols such as glycerol and up to 3% of polyoxyethylene-polyoxypropylene nonionic surfactants. Other patents such as U.S. Pat. No. 4,302,441 (Muhlemann et al) recommend that solid oral preparations comprising urea hydrogen peroxide be formulated without glycerol so as to be more effective against microorganisms on teeth. Glycerol was said to inhibit saliva and components thereof from beneficially decomposing the peroxide.

Oral compositions containing both a peroxide and sodium bicarbonate have been acclaimed by the dental profession, especially through the work of Keyes. See Keyes et al "Periodontics and Oral Hygiene", Jan. 1978, pages 51–56. Unfortunately, formulations based on the Keyes technology are particularly prone to decomposition. Several approaches have been reported to overcome difficulties presented by such combination of ingredients. U.S. Pat. No. 3,577,521 (Scheller) discloses use of acid salts in combination with alcohol-silica gels to obtain a foaming storage-stable toothpaste of peroxide-bicarbonate. U.S. Pat. No. 4,837,008 (Rudy et al) overcomes the problem through a non-aqueous dentifrice wherein an inorganic peroxide and/or bicarbonate is coated with a water-soluble barrier which is insoluble in the dentifrice vehicle.

U.S. Pat. No. 4,130,501 (Lutz) describes stable viscous hydrogen peroxide solutions formulated with Carbopol ® thickener, a polyoxyethylene-polyoxypropylene surfactant and a neutralizing agent to raise pH between 4.5 and 8.

A physical separation into separate compartments of the peroxide from co-reactive ingredients has been another approach to the problem. U.S. Pat. No. 4,849,213 and U.S. Pat. No. 4,528,180 both to Schaeffer disclose a dual-compartment package with gel and paste components, respectively. The gel component includes hydrogen peroxide, a Carbopol ® type thickener, a nonionic cellulose and a basic neutralizing agent with pH maintained at about 3–6.

U.S. Pat. No. 4,895,721 (Drucker) has focused both on the problem of viscosity and peroxide loss. Prevention of these problems is achieved through a gel base of 35–95% polyol (e.g. glycerol), and 0.75–5% gelling agent (e.g. Carbopol ®), and 0.05–1% antioxidant or U.V. absorber with pH maintained at 3.5–6.5.

U.S. Pat. No. 4,343,785 (Schmolka) discloses a gel dentifrice containing a cogeneric mixture of polyoxybutylene-polyoxyethylene block copolymers (Pluronic ® type) which may contain glycerol and be pH adjusted with citric acid. The combination is reported as retarding plaque formation and growth. The gel structure is retained even below 20° C.

From all of the aforementioned art, it is apparent that hydrogen peroxide compositions should be formulated as simply as possible to minimize potential interactions between the peroxide and the remaining ingredients. Notwithstanding such precautions, gels can lose viscosity turning into the fluid state as temperature decreases. Except for U.S. Pat. No. 4,343,785, the literature has not appreciated that dental gels based on Pluronic ® type formulations suffer from low temperature gel structure loss. This situation is rendered more difficult when a peroxide is formulated with the product. Even further difficulties arise where the peroxide gel is packaged within an expandable pump dispenser. At temperatures below 10° C., gel consistency is lost, the product turns liquid and then leaks out of the dispenser.

Accordingly, it is an object of the present invention to provide a peroxide containing gel composition that maintains structure even at temperatures below 10° C.

A further objective of the present invention is to provide a peroxide containing gel composition which under low temperature conditions remains confined to a pump dispenser package.

Another object of the present invention is to provide a gel composition of exceptional clarity.

A still further objective of the present invention is to achieve all of the above in combination with retaining a high peroxide stability.

These and other objects of the present invention will become more readily apparent upon consideration of the more detailed description and Examples which follow.

SUMMARY OF THE INVENTION

An oral composition is provided comprising:

(i) about 0.1 to about 10% by weight of a peroxygen compound;

(ii) from more than 30% to less than 50% by weight of glycerol; and (iii) a polyoxyethylene-polyoxypropylene copolymer in an amount so that a weight ratio of glycerol to copolymer ranges from 1:0.7 to 1:0.4, and the composition has a cohesion value ranging from 100 to 360 g.

Advantageously, the oral composition will contain hydrogen peroxide as the peroxygen compound and be present in a form of a clear gel composition. Best results may be obtained when pH of the composition is held to less than 3.0.

DETAILED DESCRIPTION

Now it has been found that there are several critical conditions required to achieve a chemically stable peroxide formulated gel produced of good low temperature physical stability. Present in the composition must be a combination of water glycerol (sometimes termed glycerin), and a polyoxyethylene-polyoxypropylene copolymer. Advantageously present may also be a phosphorus containing mineral or organic acid. Relative concentration of these components has been found to be quite critical and lying within a very narrow range.

The above noted components were chosen because they met the minimum functional requirements of the gel phase. These components also maximize the hydrogen bonding potential of the aqueous medium, thereby being a significant factor in the stabilization of hydrogen peroxide. Formulations of this invention exhibit very high stability; preparations held at elevated temperatures (105° F.) for nine months still had well in excess of 90% of the peroxide originally added.

The polyoxyethylene-polyoxypropylene copolymers of this invention are most suitable where the hydrophobic portion, represented by ($C_3H_6O$), has a molecular weight ranging from about 2,750 to 4,000 and the hydrophilic portion, represented by ($C_2H_4O$), constitutes about 70-80% of the weight of the copolymer. Commercially the copolymers are available from the BASF Corporation under the trademark, Pluronic F88, F99, F108 and F127. Most preferred is Pluronic F127 (hereinafter referred to by its CTFA name, Poloxamer 407) which has a molecular weight ranging from about 10,000 to 15,000, and containing about 70% of the hydrophilic polyoxyethylene moiety. Amounts of the copolymer can range anywhere from 18-25% by weight, preferably between 19 and 24%. Poloxamers are particularly suitable for this invention because of their wide pH tolerance, high compatibility with hydrogen peroxide and unique gel properties.

Below 45° F. the Poloxamer copolymers, however, do not form a gel structure in water, probably due to the reduced solubility of the hydrophobic portion. Indeed, manufacturers of the copolymer report in their literature that general formulations are best prepared below 45° F., where the water-like viscosity liquid phase is easy to process, package and fill. As the temperature rises above 45° F., the thermo-reversible gel forms in the pack. Gel transition occurs rapidly, in a matter of minutes, and normally does not adversely effect the product as both liquid and gel phases are completely homogeneous and stable. Nevertheless, there are many concerns with the loss of viscosity at low temperatures. For instance, the gel/liquid transition during winter months might be crossed many times before the end use of the product. Furthermore, as often happens with dentrifice products, they may be left overnight next to a bathroom window, exposing them to temperatures below 45° F. Finally, in situations where the package designed for this product is based upon a toothpaste pump, the piston seals may not retain the low viscosity liquid phase.

Based on the above considerations, it is important to formulate a gel that avoids low temperature liquification, while still maintaining good storage stability.

A combination of Poloxamer and glycerol, in special ratio, has been found which accomplishes both purposes. The Poloxamer component stabilizes the peroxide while the glycerol inhibits liquification of the Poloxamer at the low temperature.

The glycerol must be present in an amount greater than 30% and less than 50%, preferably from about 35% to 45%, optimally about 40% by weight.

Critical for the invention is that the weight ratio of glycerol to the polyoxyethylene-polyoxypropylene copolymers be within the narrow range from 1:0.7 to 1:0.4, preferably between 1:0.6 and 1:0.45, optimally about 1:0.5.

Advantageously, the compositions of this invention will be maintained at a low pH, preferably a pH of less than 3, optimally being of pH no higher than 2.8. While there is no set lower end of the pH range, for practical reasons pH of the composition will not be less than about 0.0 and usually not less than 2.0. Acidification is best accomplished through use of a phosphorous-based inorganic or organic acid. Most effective is phosphoric acid.

Water will be present in the compositions in amounts ranging from about 35% to about 55%, preferably between about 40% to 50% by weight.

A variety of water-soluble peroxygen compounds, such as sodium perborate, persilicate, perphosphate and hydrogen peroxide, may be employed. The most suitable for this invention is hydrogen peroxide itself. The amount of the peroxygen compound may range from about 0.1 to about 10% by weight. In terms of active weight hydrogen peroxide, the amount will range from about 0.5% to about 3%, preferably from about 0.8% to about 1.8%, optimally between about 1% and 1.5% by weight.

Adjunct minor ingredients may also be present in the composition of this invention. Included may be small amounts of colorant, and antioxidant. Thickeners, such as cross-linked polyacrylates, e.g. Carbopol $^R$, flavors and cellulosic or other gums will normally be absent to avoid interaction with the peroxide.

The following examples will more fully illustrate the embodiments of this invention. All parts, percentages and proportions referred to herein and in the appended claims are by weight unless otherwise illustrated.

EXAMPLE 1

This example reports evidence of the glycerol: Poloxamer ratio and Poloxamer level necessary to achieve viscosity retention at low temperatures. A series of formulations were prepared incorporating 4.285% hydrogen peroxide (35% active, food grade), 1% phosphoric acid (12.75% active wt/wt), and variable levels of deionized water, Poloxamer 407 and glycerol. These components were blended together forming a 1.5% hydrogen peroxide clear gel.

Tables I–III set forth the effects of varying the ratio of glycerol to Poloxamer 407 as relates to gelation temperature.

TABLE I

Effect of Glycerol at Constant (25%) Poloxamer 407

| Poloxamer 407% | 25 | 25 | 25 | 25 |
|---|---|---|---|---|
| Glycerol % | 10 | 20 | 25 | 50 |
| G:P Ratio | 1:2.5 | 1:1.25 | 1:1 | 2:1 |
| Gellation Temp. F. | 51 | 32 | 9 | No gel |
| Viscosity (cohesion g) | 250 | >360 | >360 | — |

TABLE II

Effect of Glycerol at Constant (20%) Poloxamer 407

| Poloxamer 407% | 20 | 20 | 20 | 20 | 20 | 20 | 20 | 20 |
|---|---|---|---|---|---|---|---|---|
| Glycerol % | 10 | 20 | 30 | 35 | 40 | 42.5 | 45 | 50 |
| G:P Ratio | 1:2 | 1:1 | 1:0.67 | 1:0.57 | 1:0.5 | 1:0.47 | 1:0.44 | 1:0.4 |
| Gellation Temp. F. | 65 | 45 | 21 | 11 | 5 | 0 | −1 | 55 |
| Viscosity (cohesion g) | 55 | 175 | 230 | 240 | 230 | 280 | 280 | 95 |

TABLE III

Effect of Poloxamer at Constant Glycerol (20%) (40%) (50%)

| Poloxamer 407% | 20 | 25 | 27.5 | 30 | 32.5 | 17.5 | 20 | 15 | 20 | 25 |
|---|---|---|---|---|---|---|---|---|---|---|
| Glycerol % | 20 | 20 | 20 | 20 | 20 | 40 | 40 | 50 | 50 | 50 |
| G:P Ratio | 1:1 | 1:1.25 | 1:1.38 | 1:1.5 | 1:1.63 | 1:0.44 | 1:0.5 | 1:0.3 | 1:0.4 | 1:0 |
| Gellation Temp. F. | 45 | 32 | 23 | 15 | <3 | 20 | 5 | No gel* | 55 | No gel* |
| Viscosity (cohesion g) | 175 | 335 | >360 | >360 | >360 | <100 | 230 | <100 | 95 | <100 |

*Much greater than 70° F.

From Table I it can be seen that increasing the glycerol level advantageously lowers the temperature of gelation. However, there were two problems. The gels formed were extremely "hard" as indicated by the high viscosities (measured as the force in grams required to pull apart two plates sandwiching a uniform thickness of the gel). In fact, the gels were too hard to be processable by conventional toothpaste industry means. The upper range is usually set at 250 g, although processability is probably possible up to 300 g. Secondly, the gels could not be prepared at high glycerol concentrations; an attempt to make a gel with a Glycerol:Poloxamer (G:P) ratio of 2:1 (at 25% Poloxamer) was unsuccessful. The Poloxamer would not completely hydrate in 50% glycerol.

The aforementioned experiments were repeated at 20% Poloxamer where a similar trend was followed. See Table II. These results clearly demonstrated that gelation temperatures can be lowered by increasing glycerol content of the gel. The gels formed were softer and fell within the processable range. The G:P ratio of 1:0.5 (at 20% Poloxamer) was identified as the optimum. At this level the gel had low enough gelation temperature (5° F.) to minimize liquification problems and allow a formulation safety margin below the higher (45–50%) glycerol levels where the trend failed and gelation temperatures rose again. There was an added benefit in the 1:0.5 (G:P) ratio formulation in that the liquid phase below 0°–3° F. had a quite high "honey-like" viscosity which also did not leak from a pump package.

In order to assess whether another optimum low gelation temperature could be achieved at other Poloxamer loadings, the experiment was repeated at 20, 40 and 50% glycerol. Table III reports the gelation temperature as a function of Poloxamer level for these three levels of glycerol. The results indicate that at lower (20%) glycerol levels, low gelation temperatures can be achieved. However, to achieve gelation temperatures down below 10° F., the Poloxamer level needed to be raised to 35% where the gels produced were far too "hard" (cohesions well in excess of 360 g) to be readily processed. At 40% glycerol, there was a similar trend. Attempts to prepare gels at 50% glycerol were not very successful. The data suggests that there was too little water to hydrate the Poloxamer (@25%) and too little Poloxamer (@15%) to form stable gels. This is similar to the trend in Table II where, in the 45–50% glycerol range, the nature of the formulation changes and gelation temperature is no longer reduced by increasing glycerol.

Based upon the foregoing experiments, it is concluded that Poloxamer gels formulated at a G:P of about 1:0.5 (20% Poloxamer loading), exhibit good low temperature gel stability and can be readily processed.

EXAMPLE 2

Study of pH and Acid Choice

Table IV demonstrates how the pH of the gel, adjusted by phosphoric acid content, has effects upon peroxide stability. The pH needed to be maintained below 3.0, especially at 2.8 or less to maximize stability. Nominal pH of the formula evaluated under Table II was 2.5. Hydrochloric acid completely destabilized the peroxide gel. Neither nitric nor citric acids met the >80% stability criteria, although the stability of these gels were better than that containing hydrochloric acid.

TABLE IV

Effect of Gel pH on Hydrogen Peroxide Stability (Phosphoric Acid)

| pH | PSST Stability % |
|---|---|
| 6.35 | 29 |
| 5.9 | 36 |
| 5.7 | 31 |
| 4.25 | 37 |
| 4.1 | 36 |
| 3.84 | 32 |
| 3.6 | 36 |
| 3.48 | 39 |
| 3.29 | 32 |
| 3.03 | 59 |
| 2.72 | 100 |

Testing Methods

Hydrogen peroxide: The majority of the hydrogen peroxide studies were undertaken as accelerated storage studies at 105° F. The criteria for stable product required >80% of the peroxide remaining after three months. The peroxide level was measured in the standard way by oxidizing potassium iodide to iodine and titrating with sodium thiosulphate on an auto-titrator fitted with a redox electrode.

In order to speed up the information feedback loop on peroxide stability a high temperature (203° F.) short time (6 hours) test was developed which demonstrated good correlation with the 105° F. storage. This fast test has been called the Peroxide Stability/Stress Test (PSST). The peroxide content of the gel was assayed as described above, and assessed against the same criteria.

Gelation Temperature: This was measured by cooling down the gel well into the liquid phase state. The liquid was then allowed to warm slowly at room temperature until the gel began to reform. The temperature taken at this point was the gelation temperature.

The foregoing description and examples illustrated selected embodiments of the present invention. In light thereof, various modifications will be suggested to one skilled in the art, all of which are within the spirit and purview of this invention.

What is claimed is:

1. An oral composition comprising:
   (i) about 0.1 to about 10% by weight of a peroxygen compound;
   (ii) from more than 30% to less than 50% by weight of glycerol; and
   (iii) a polyoxyethylene-polyoxypropylene copolymer in an amount so that a weight ratio of glycerol to copolymer ranges from 1:0.7 to 1:0.4, the composition having a cohesion value ranging from 100 to 360 g and having a pH of less than 3.03.

2. An oral composition according to claim 1, wherein glycerol is present from 35% to 45% by weight.

3. An oral composition according to claim 1, wherein the polyoxyethylene-polyoxypropylene copolymer is present from 18% to 25% by weight.

4. An oral composition according to claim 1, wherein the weight ratio of glycerol to copolymer ranges from 1:0.6 to 1:0.44.

5. An oral composition according to claim 1, wherein the pH is no higher than 2.8.

6. An oral composition according to claim 5, wherein a low pH is maintained with a phosphorus type organic or inorganic acid.

7. An oral composition according to claim 6, wherein the acid is phosphoric acid.

8. An oral composition according to claim 1, held within a pump package.

9. An oral composition according to claim 1, wherein thickening agents other than copolymer and glycerol are absent.

10. An oral composition according to claim 1, further comprising colorants present in an effective amount to impart a color to the composition.

11. An oral composition according to claim 1, wherein the composition is in the form of a gel.

12. An oral composition according to claim 11, wherein the gel is transparent.

* * * * *